(12) United States Patent
Stinson et al.

(10) Patent No.: US 6,183,508 B1
(45) Date of Patent: Feb. 6, 2001

(54) METHOD FOR TREATING A VESSEL WITH A TITANIUM ALLOY STENT

(75) Inventors: Jonathan S. Stinson, Plymouth; Claude O. Clerc, Eden Prairie; David W. Mayer, Bloomington, all of MN (US)

(73) Assignee: Schneider Inc, Maple Grove, MN (US)

( * ) Notice: Under 35 U.S.C. 154(b), the term of this patent shall be extended for 0 days.

(21) Appl. No.: 09/190,716

(22) Filed: Nov. 12, 1998

Related U.S. Application Data

(62) Division of application No. 08/874,780, filed on Jun. 13, 1997, now Pat. No. 5,888,201, which is a continuation of application No. 08/598,751, filed on Feb. 8, 1996, now abandoned.

(51) Int. Cl.⁷ .............................. A61F 2/06; A61M 29/00

(52) U.S. Cl. .............................. 623/1.2; 604/96; 604/104; 606/108; 606/194; 606/198

(58) Field of Search .................................. 623/1, 11, 12, 623/1.2; 604/96, 104; 606/108, 194, 195, 198

(56) References Cited

U.S. PATENT DOCUMENTS

| | | | |
|---|---|---|---|
| 4,994,071 | * | 2/1991 | MacGregor .................. 606/194 |
| 5,064,435 | * | 11/1991 | Porter ............................ 623/1 |
| 5,477,864 | * | 12/1995 | Davidson ...................... 128/657 |

* cited by examiner

*Primary Examiner*—V. Millin
*Assistant Examiner*—Choon P. Koh
(74) *Attorney, Agent, or Firm*—Faegre & Benson LLP

(57) ABSTRACT

A method for treating a body vessel using a stent formed from filaments of titanium or titanium alloys such as Ti—13Zr—13Nb.

25 Claims, 9 Drawing Sheets

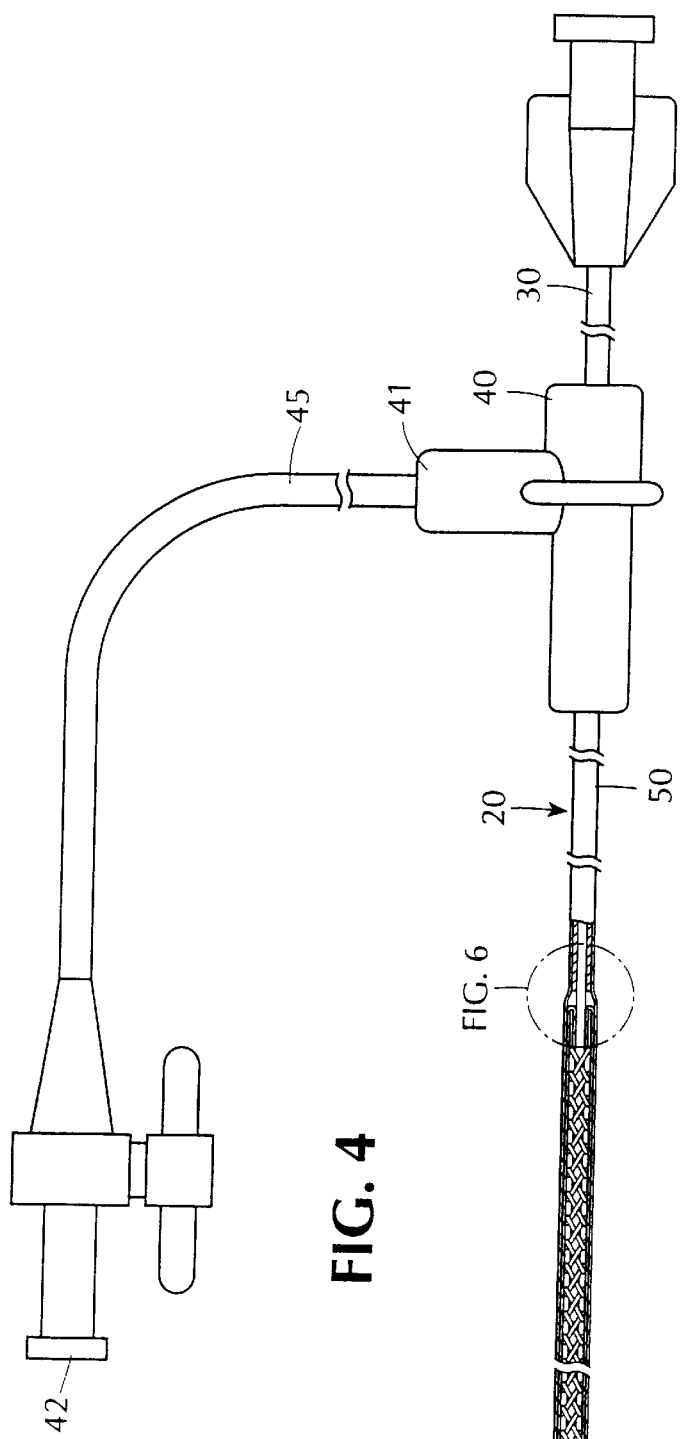
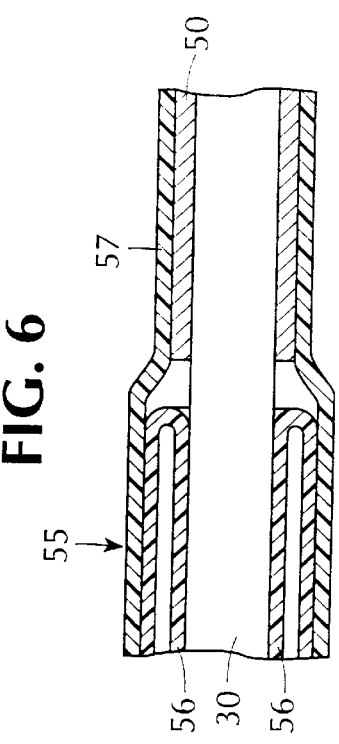
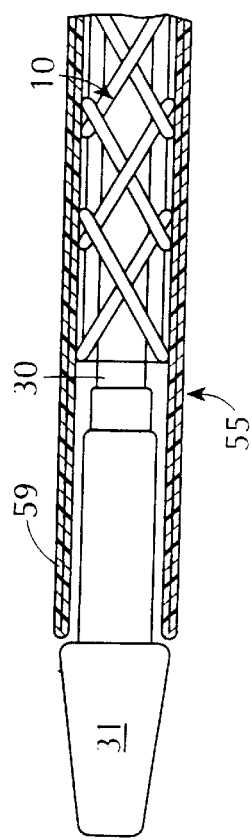

FIG. 13

| STENT O.D (IN.) | #1A AS-BRAIDED FORCE (LB.) | #2 AS-BRAIDED FORCE (LB.) | #3 AS-BRAIDED FORCE (LB.) | #1 DIFF. HARDENED FORCE (LB.) | #2 DIFF. HARDENED FORCE (LB.) | #3 DIFF. HARDENED FORCE (LB.) | ELGILOY /DFT FORCE (LB.)(1) | ELGILOY FORCE (LB.)(2) |
|---|---|---|---|---|---|---|---|---|
| 0.2000 | 0.0257 | 0.0352 | 0.0342 | 0.0804 | 0.0847 | 0.0881 | 0.165 | 0.154 |
| 0.2204 | 0.0211 | 0.0305 | 0.0303 | 0.0696 | 0.0739 | 0.0775 | | |
| 0.2407 | 0.0172 | 0.0263 | 0.0264 | 0.0635 | 0.0668 | 0.0666 | | |
| 0.2611 | 0.0132 | 0.0222 | 0.0212 | 0.0571 | 0.0591 | 0.0632 | | |
| 0.2815 | 0.0083 | 0.0185 | 0.0171 | 0.0505 | 0.0549 | 0.0547 | 0.096 | 0.099 |
| 0.3019 | 0.0039 | 0.0142 | 0.0137 | 0.0478 | 0.0483 | 0.0477 | | |
| 0.3222 | 0.0005 | 0.0099 | 0.0090 | 0.0414 | 0.0433 | 0.0434 | | |
| 0.3426 | 0.0001 | 0.0041 | 0.0035 | 0.0343 | 0.0367 | 0.0313 | | |
| 0.3630 | 0.0001 | 0.0003 | 0.0001 | 0.0264 | 0.0288 | 0.0244 | 0.022 | 0.022 |
| 0.3833 | 0.0000 | 0.0000 | 0.0000 | 0.0148 | 0.0198 | 0.0157 | | |
| 0.4037 | 0.0000 | 0.0000 | 0.0000 | 0.0021 | 0.0075 | 0.0031 | | |
| 0.4241 | | | | | 0.0002 | | | |
| 0.4445 | | | | | 0.0001 | | | |

RADIAL FORCE TEST

METHOD FOR TREATING A VESSEL WITH A TITANIUM ALLOY STENT

REFERENCE TO RELATED APPLICATION

This application is a divisional of application Ser. No. 08/874,780 filed on Jun. 13, 1997, U.S. Pat. No. 5,888,201, which is a continuation of application Ser. No. 08/598,751 filed on Feb. 8, 1996, abandoned and which is hereby incorporated by reference in its entirety.

BACKGROUND OF THE INVENTION

1. Field of the Invention

The present invention relates generally to the treatment of body vessels through the use of implantable, radially expandable medical prostheses which are frequently referred to as stents. In particular, the present invention is a method which uses a titanium alloy stent.

2. Description of the Related Art

Medical prostheses frequently referred to as stents are well known and commercially available. They are, for example, disclosed generally in the Wallsten U.S. Pat. No. 4,655,771, the Wallsten et al. U.S. Pat. No. 5,061,275 and in International Application Publication Number WO 94/24961, all of which are hereby incorporated by reference in their entirety. Devices of these types are used within body vessels of humans and other animals for a variety of medical applications. Examples include intravascular stents for treating stenosis, stents for maintaining openings in the urinary, biliary, esophageal and renal tracts and vena cava filters to counter emboli.

Briefly, self-expanding stents of the type described in the above-identified patent documents are formed from a number of resilient filaments which are helically wound and interwoven in a braided configuration. The stents assume a substantially tubular form in their unloaded or expanded state when they are not subjected to external forces. When subjected to inwardly directed radial forces the stents are forced into a reduced-radius and extended-length loaded or compressed state. A delivery device which retains the stent in its compressed state is used to deliver the stent to a treatment site through vessels in the body. The flexible nature and reduced radius of the compressed stent enables it to be delivered through relatively small and curved vessels. After the stent is positioned at the treatment site the delivery device is actuated to release the stent, thereby allowing the stent to self-expand within the body vessel. The delivery device is then detached from the stent and removed from the patient. The stent remains in the vessel at the treatment site.

Stents must exhibit a relatively high degree of biocompatibility since they are implanted in the body. Commonly used materials for the stent filaments include Elgiloy® and Phynox® spring alloys. Elgiloy® alloy is available from Carpenter Technology Corporation of Reading, Pa. Phynox® alloy is available from Metal Imphy of Imphy, France. Both of these metals are cobalt-based alloys which also include chromium, iron, nickel and molybdenum. Other materials used for self-expanding stent filaments are 316 stainless steel and MP35N alloy which are available from Carpenter Technology Corporation and Latrobe Steel Company of Latrobe, Pa., and superelastic Nitinol nickel-titanium alloy which is available from Shape Memory Applications of Santa Clara, Calif. Nitinol alloy contains about 45% titanium. Yet another self-expanding stent, available from Schneider (USA) Inc. of Minneapolis, Minn., includes an Elgiloy® alloy case with a tantalum or platinum alloy core. The tantalum or platinum alloy core is radiopaque and enhances the visibility of the stent in fluoroscopy during implantation.

The strength and modulus of elasticity of the filaments forming the stents are also important characteristics. Elgiloy®, Phynox®, MP35N and stainless steel are all high strength and high modulus metals. Nitinol has relatively lower strength and modulus.

There remains a continuing need for self-expanding stents with particular characteristics for use in various medical indications. Stents are needed for implantation in an ever growing list of vessels in the body. Different physiological environments are encountered and it is recognized that there is no universally acceptable set of stent characteristics. In particular, there is a need for stents formed from moderate strength materials having lower moduli of elasticity than those of Elgiloy®, Phynox®, MP35N, and stainless steel from which certain stents are currently formed. Stents formed from moderate strength and relatively low moduli of elasticity materials would have properties adapted to an expanded range of treatment applications. Stents with lower moduli of elasticity material would be less stiff and more flexible than a stent made of the same size wire and same design utilizing a high modulus material. Stents of these types must also exhibit a high degree of biocompatibility. Furthermore, the filaments from which the stent is fabricated are preferably radiopaque to facilitate their implantation into patients.

The current self-expanding stents made of Elgiloy®, MP3N, stainless steel, and nitinol can be made to have various characteristics by varying filament wire sizes and stent designs. However, a group of stent wire materials with properties between those of very high strength, high modulus materials (Elgiloy®, MP35N, stainless steel) and of low strength, low modulus materials (nitinol) would allow even more stent variants to be produced. The implantation of an intraluminal stent will preferably cause a generally reduced amount of acute and chronic trauma to the luminal wall while preforming its function. A stent that applies a gentle radial force against the wall and that is compliant and flexible with lumen movements is preferred for use in diseased, weakened, or brittle lumens. The stent will preferably be capable of withstanding radially occlusive pressure from tumors, plaque, and luminal recoil and remodeling.

BRIEF DESCRIPTION OF THE DRAWINGS

FIG. 4 is a side view of a delivery device with the stent shown in FIG. 1 loaded thereon.

FIG. 5 is a detailed view of the portion of the delivery device encircled at 5 in FIG. 4.

FIG. 6 is a detailed view of the portion of the delivery device encircled at 6 in FIG. 4.

FIG. 13 is a table of hoop force test results for three braided structures and three heat-treated prototype stents, all formed from 0.18 mm Ti—13Nb—13Zr wire and formed on a 12 mm mandrel at a 110° braid angle. Test results for similarly sized Elgiloy® and Elgiloy®/DFT stents are also tabulated for purposes of comparison.

DETAILED DESCRIPTION OF THE PREFERRED EMBODIMENTS

Figure 1:
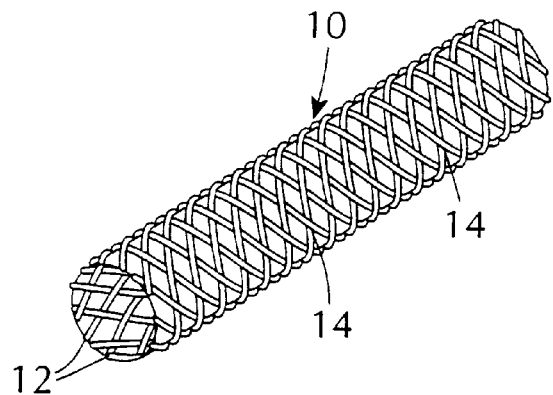
FIG. 1 is an isometric view of a stent in accordance with the present invention, illustrating the braided configuration of the filaments.
Figure 2:
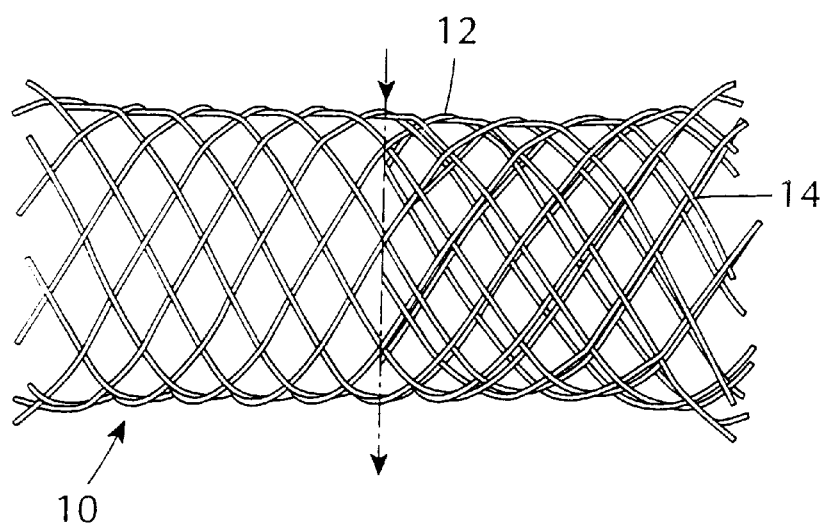
FIG. 2 is a partial longitudinal cross-sectional view of the stent shown in FIG. 1.

An implantable prosthesis or stent 10 which can be used in accordance with the present invention is illustrated generally in FIGS. 1 and 2. Stent 10 is a tubular device formed from two sets of oppositely-directed, parallel, spaced-apart and helically wound elongated strands or filaments 12. The sets of filaments 12 are interwoven in an over and under braided configuration intersecting at points such as 14 to form an open mesh or weave construction. As described in greater detail below, at least one and preferably all filaments 12 consist of commercially available grades of pure titanium or titanium alloys including at least about sixty-eight weight percent titanium. Methods for fabricating stents 10 are generally known and disclosed, for example, in the Wallsten U.S. Pat. No. 4,655,771 and the Wallsten et al. U.S. Pat. No. 5,061,275, which are hereby incorporated by reference in their entirety.

Stent 10 is shown in its expanded or relaxed state in FIGS. 1 and 2, i.e., in the configuration it assumes when subject to no external loads or stresses. The filaments 12 are resilient, permitting the radial compression of stent 10 into a reduced-radius, extended-length configuration or state suitable for delivery to the desired placement or treatment site through a body vessel (i.e., transluminally). Stent 10 is also self-expandable from the compressed state, and axially flexible. As an example, one embodiment of stent 10 has a diameter of about 10 mm (0.39 inches) in the relaxed state, and is capable of being elastically compressed to a diameter of about 2 mm (0.08 inches). The stent described in this example has an axial length in its compressed state which is about twice its axial length in the relaxed state.

Stated another way, stent 10 is a radially and axially flexible tubular body having a predetermined diameter that is variable under axial movement of the ends of the body relative to each other. The stent 10 is composed of a plurality of individually rigid but flexible and elastic thread elements or filaments 12, each of which extends in a helix configuration along a longitudinal center line of the body as a common axis. At least one and preferably all of filaments 12 consist of commercially available grades of pure titanium or titanium alloys including at least about sixty-eight weight percent titanium. The filaments 12 define a radially self-expanding body. The body is provided by a first number of filaments 12 having a common direction of winding but axially displaced relative to each other, and crossing a second number of filaments 12 also axially displaced relative to each other but having an opposite direction of winding.

Figure 3:
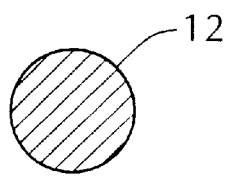
FIG. 3 is a cross-sectional view of one of the filaments of the stent shown in FIG. 1.
Figure 7:
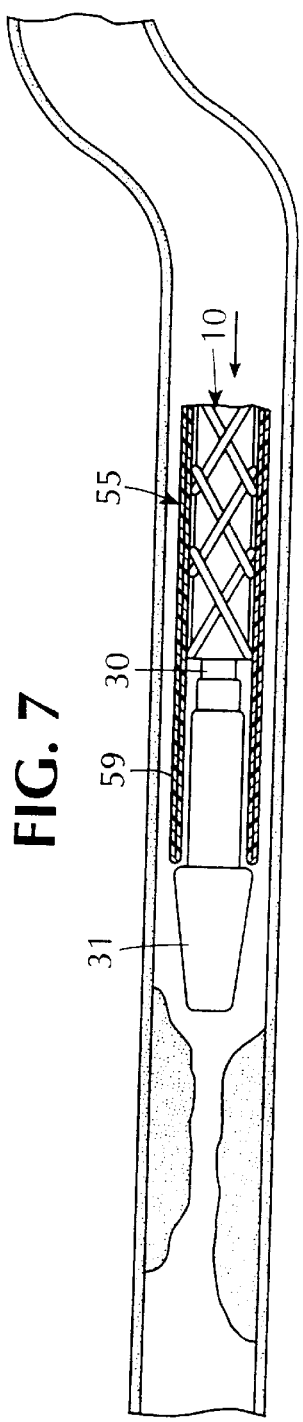
FIGS. 7–10 are partial cross-sectional side views of the distal portion of the delivery device and stent shown in FIG. 4 at various stages during a stent deployment operation in a body vessel.
Figure 8:
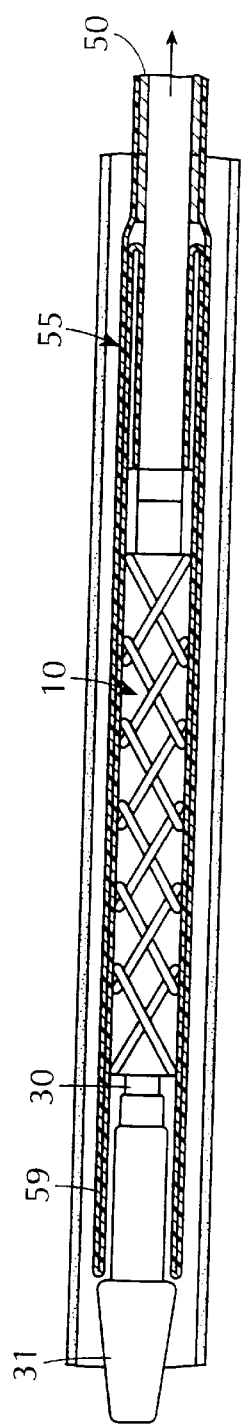
Figure 9:
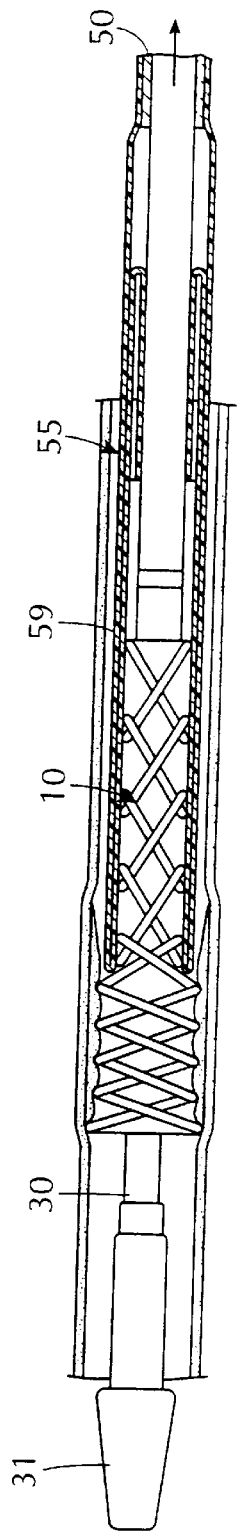
Figure 10:
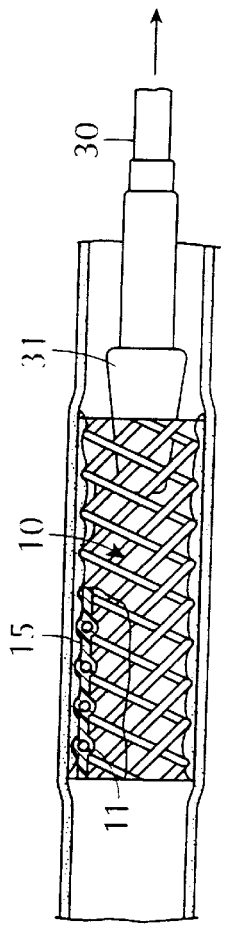

The tubular and self-expandable body or structure formed by the interwoven filaments 12 is a primary prosthetically-functional structure of stent 10, and for this reason the device can be considered to substantially consist of this structure to the exclusion of other structures. However, it is known that other structures and features can be included in stents, and in particular features which enhance or cooperate with the tubular and self-expandable structure or which facilitate the implantation of the structure. One example is the inclusion of radiopaque markers on the structure which are used to visualize the position of the stent through fluoroscopy during implantation. Another example is the inclusion of a covering or additional interwoven filaments, for instance, to reduce the porosity or open spaces in the structure so that the stent can be used to prevent tissue ingrowth or be used as a graft. Other examples include collapsing threads or other structures to facilitate repositioning and removal of the stent. Stents of these types nonetheless still substantially consist of the tubular and self-expandable structure formed by interwoven filaments 12 and shown in FIGS. 1 and 2. Furthermore, many of the desirable features and properties of stent 10 will be present if some, but not all, of the filaments 12 consist of titanium or titanium alloy FIG. 3 is a cross-sectional view of one of the titanium or titanium alloy filaments 12. As shown, the filaments 12 are substantially homogeneous in cross section. Commercially available alloys may have minor fluctuations in component concentration while remaining substantially homogeneous. Filaments 12 are also homogeneous in length. The filaments 12 can be formed from titanium and a wide variety of titanium alloys containing at least sixty-eight weight percent titanium, preferably about 68 to about 96 weight percent, and more preferably about 73 to about 86 weight percent. Titanium and other alloy compositions described throughout the remainder of this description in percentages are given in weight percentages.

EXAMPLE 1

A prototype stent 10 was fabricated from about 0.18 mm (0.007 inch) diameter filaments 12 of a titanium alloy containing about 74% titanium, 13% niobium and 13% zirconium (Ti—13Nb—13Zr). The wire from which the filaments were fabricated was drawn by G&S Titanium of Wooster, Ohio, from a rod of Ti—13Nb—13Zr alloy supplied by Smith & Nephew Richards Inc. of Memphis, Tenn. The wire was acid cleaned, had about 52% cold work, and its diameter varied between about 0.164 mm (0.00635 inches) and about 0.184 mm (0.00715 inches). Portions of the Ti—13Nb—13Zr wire were heat treated by Smith & Nephew Richards Inc. using a diffusion hardening treatment. Samples of the as-drawn and heat-treated wire were tested for tensile strength, U-bend wire spin fatigue, bend modulus and torsion/shear (rigidity) modulus.

The as-drawn wire samples were measured to have a mean ultimate tensile strength of about 1034 MPa (150 ksi), mean 0.2% offset yield strength of about 972 MPa (141 ksi), mean elongation of 3.1% and mean elastic modulus of about 48,265 MPa (7.0 msi). The heat-treated wire samples were measured to have a mean ultimate tensile strength of about 1048 MPa (152 ksi), mean 0.2% offset yield strength of about 1007 MPa (146 ksi), mean elongation of 2.4% and mean elastic modulus of about 73,087 MPa (10.6 msi). For purposes of comparison, samples of superelastic Nitinol wire having a 0.13 mm (0.005 inch) diameter were found to have a mean ultimate tensile strength of about 1420 MPa (206 ksi), mean 0.2% offset yield strength of about 517 MPa (75 ksi), mean elongation of 14.4% and mean elastic modulus of about 37,233 MPa (5.4 msi). Aged Elgiloy® wire having a 0.17 mm (0.0067 inch) diameter had a mean ultimate tensile strength of about 2,841 MPa (412 ksi), mean 0.2% offset yield strength of about 2627 MPa (381 ksi), mean elongation of 1.9% and mean elastic modulus of about 191,681 MPa (27.8 msi).

Figure 11:
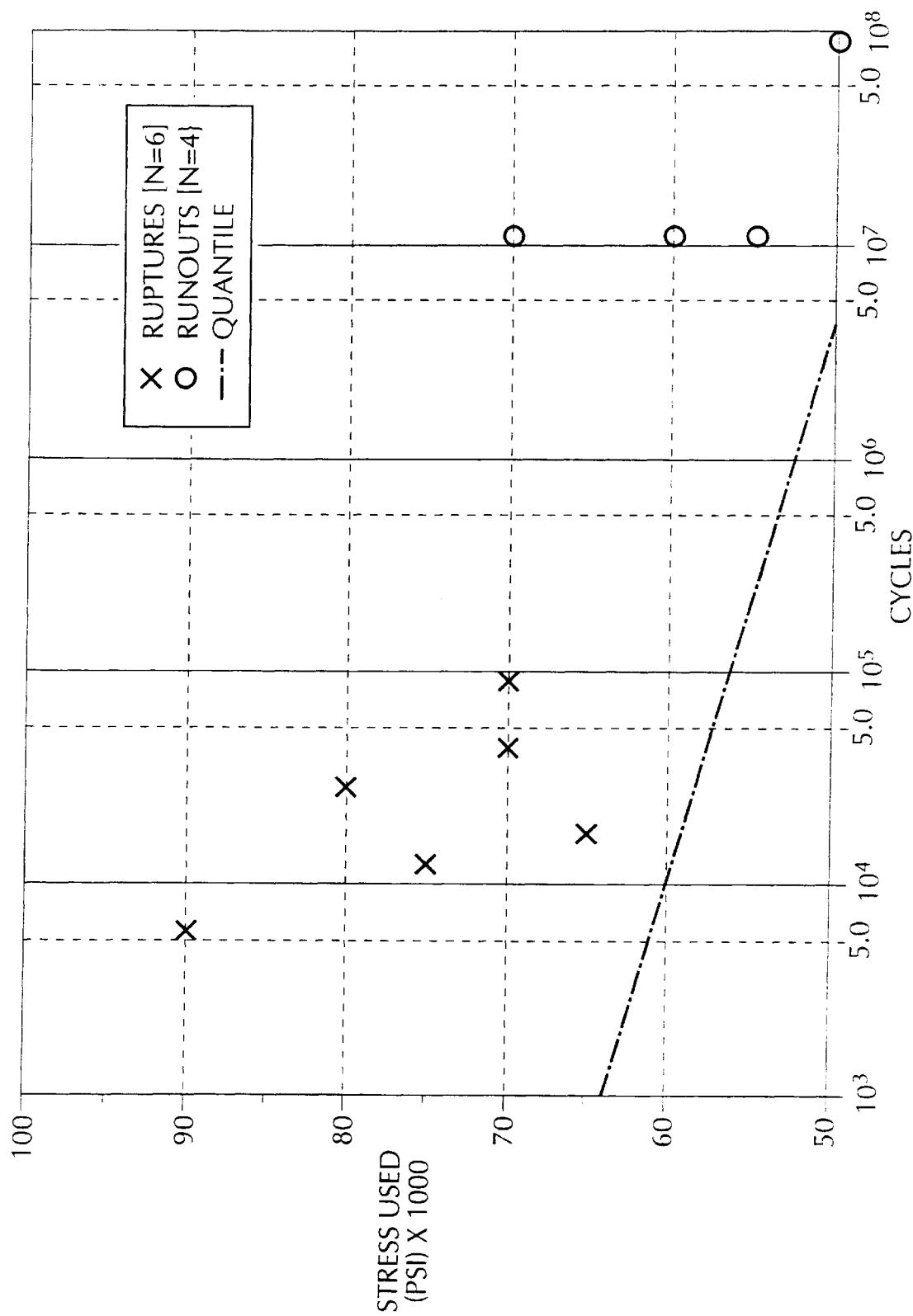
FIG. 11 is a graph of U-bend wire spin fatigue test results on ten samples of as-drawn 0.18 mm Ti—13Nb—13Zr wire.
Figure 12:
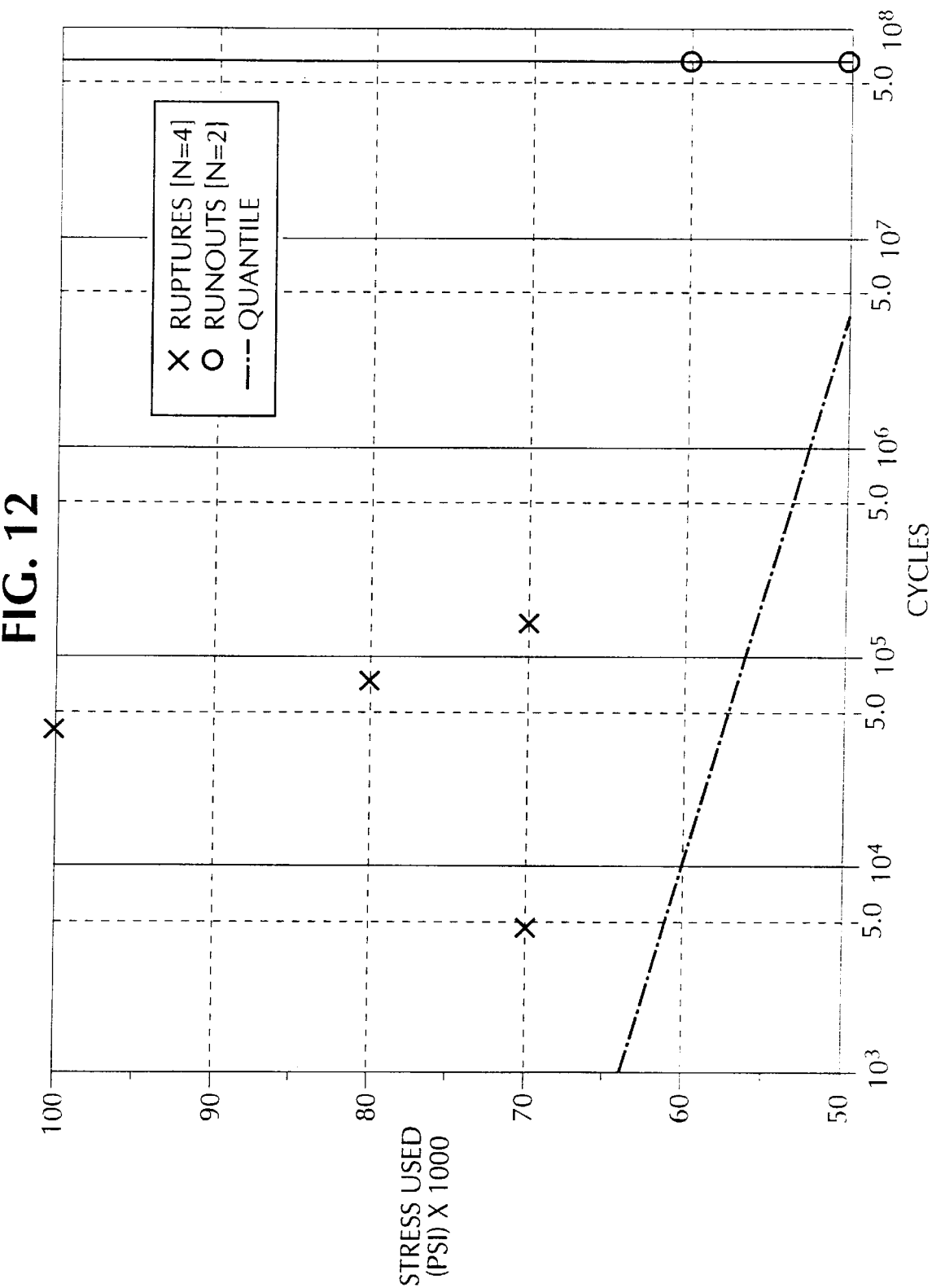
FIG. 12 is a graph of U-bend wire spin fatigue test results on six samples of heat-treated 0.18 mm Ti—13Nb—13Zr wire.

The fatigue tests on both the as-drawn and heat-treated wire resulted in a number of samples that achieved ten million cycle run-outs at stress levels below about 414 MPa (60 ksi) without rupture. A number of the as-drawn samples subjected to stress levels between about 448 MPa (65 ksi) and 552 MPa (80 ksi) ruptured between about ten thousand and one hundred thousand cycles. A number of the heat-treated samples subjected to stress levels between about 483 MPa (70 ksi) and 552 MPa (80 ksi) ruptured between about five hundred and ten thousand cycles. A graph of the U-bend wire spin fatigue test results on the as-drawn wire is shown in FIG. 11. A graph of the U-bend wire spin fatigue test results on the heat-treated wire is shown in FIG. 12. For purposes of comparison, the 0.13 mm diameter superelastic Nitinol wire had a slightly lower fatigue strength, and the 0.17 mm Elgiloy® wire had a fatigue strength which was about 50% higher than the Ti—13Nb—13Zr wire.

The bend modulus of the Ti—13Nb—13Zr wire was measured to be about 38,854 MPa (5.2 msi) for the as-drawn samples, and about 61,366 MPa (8.9 msi) for the heat-treated samples. In comparison, the bend modulus is about 43,439 MPa (6.3 msi) for the 0.13 mm superelastic Nitinol wire, and about 123,421 MPa (17.9 msi) for the 0.17 mm Elgiloy® wire.

The torsion/shear modulus of the Ti—13Nb—13Zr wire was measured to be about 24,133 MPa (3.5 msi) for the as-drawn samples, and about 33,096 MPa (4.8 msi) for the heat-treated samples. In comparison, the torsion shear modulus is about 24,133 MPa (3.5 msi) for the 0.13 mm superelastic Nitinol wire, and about 93,083 MPa (13.5 msi) for the 0.17 mm Elgiloy® wire.

The prototype tubular structures formed from the Ti—13Nb—13Zr wire were produced with twenty four filaments braided around a 10 mm mandrel (12 mm diameter) at a 110° braid angle. A number of the structures were heat treated by Smith & Nephew Richards Inc. using a diffusion hardening treatment to produce the prototype stents. The heat treating process increased the stability of the devices by helping to prevent the braid from unraveling. However, whether or not the heat treating process is used will depend on the desired characteristics of the stent. The braided structures and stents were tested for hoop force.

The heat treated stents exhibited the characteristics of a braid-like tubular stent. The stent could be compressed radially and would extend axially. When the applied radial pressure was released the stent returned to its original undeformed state through elastic recoil. A stent was successfully loaded onto a 9 French size delivery device.

The average hoop force required to constrain the braided structures from their relaxed state to an outer diameter of about 5.16 mm (0.20 inch) was about 0.14N (0.0317 lb), and ranged between about 0.11N (0.0257 lb) and about 0.16N (0.0352 lb). The average hoop force required to constrain the heat treated prototype stents from their relaxed state to an outer diameter of about 5.16 mm (0.20 inch) was about 0.38N (0.0844 lb), and ranged between about 0.36N (0.0804 lb) and about 0.39N (0.0881 lb). For purposes of comparison, a similarly sized Elgiloy®/drawn filled tube (Elgiloy®/DFT) stent formed from about 0.29 mm (0.0055 inch) diameter wire having a tantalum core and an Elgiloy® case requires a force of about 0.73N (0.165 lb) to be constrained to the same diameter. A similarly sized Elgiloy® stent formed from about 0.12 mm (0.0047 inch) diameter wire requires a force of about 0.68N (0.154 lb) to be constrained to the same diameter. FIG. 13 is a tabulation of the hoop force test results for three braided structures and three heat-treated prototype stents, as well as the similarly sized Elgiloy® and Elgiloy®/DFT stents.

The tests described immediately above indicate that stents 10 fabricated from the Ti—31Nb—13Zr wire have desirable characteristics for certain applications. In particular, the stents 10 have relatively low elastic modulus and relatively moderate strength. The Ti-13-13 stent wire had a 0.2% offset, yield strength and U-bend fatigue properties between that of Elgiloy® and nitinol (two currently used stent materials). The stents had measurable resistance to compression and would be expected to exert a more gentle force (less radial force) than the Elgiloy® stent on the lumen wall. Stents 10 are therefore durable and flexible, and capable of being moved through curved vessels or lumens during delivery. The titanium alloy is highly biocompatible and is resistant to thrombosis and bacterial infection.

Although Ti—13Nb—13Zr is the most preferred titanium alloy containing niobium and zirconium, other compositions can also be used. In particular, titanium alloys consisting of at least about 68% titanium, 1–29% Nb and 1–29% Zr, including such alloys with 10–15% Nb and 10–15% Zr, will offer advantages similar to the most preferred composition.

EXAMPLES 2–6

Radial pressures were calculated for each of five Ti—6Al—4V stents 10 of varying diameters (examples 2–6, respectively). The radial pressures are those of the stents 10 at eighty-five percent of their diameter (i.e., midrange diameter). The characteristics and radial pressures of stent Examples 2–6 are set forth below in Table 1. The individual stent diameter/pressure points are shown graphically in FIG. 16, and were computer generated using mathematical formulas described in the Jedwab and Clerc article "A Study of the Geometrical and Mechanical Properties of a Self-Expanding Metallic Stent—Theory and Experiment," Journal of Applied Biomaterials, Vol. 4, pp 77–85 (1993), which is hereby incorporated by reference in its entirety.

TABLE 1

| Stent Example | Relaxed State Diameter (mm) | Number of Wires | Wire Diameter (mm) | Brand Angle (degrees) | Radial Pressure (mm Hg) |
|---|---|---|---|---|---|
| 2 | 5 | 20 | 0.09 | 110 | 36.7 |
| 3 | 8 | 24 | 0.11 | 110 | 15.5 |
| 4 | 10 | 24 | 0.14 | 105 | 13.4 |
| 5 | 16 | 30 | 0.17 | 110 | 7.1 |
| 6 | 20 | 36 | 0.17 | 120 | 5.3 |

Figure 16:
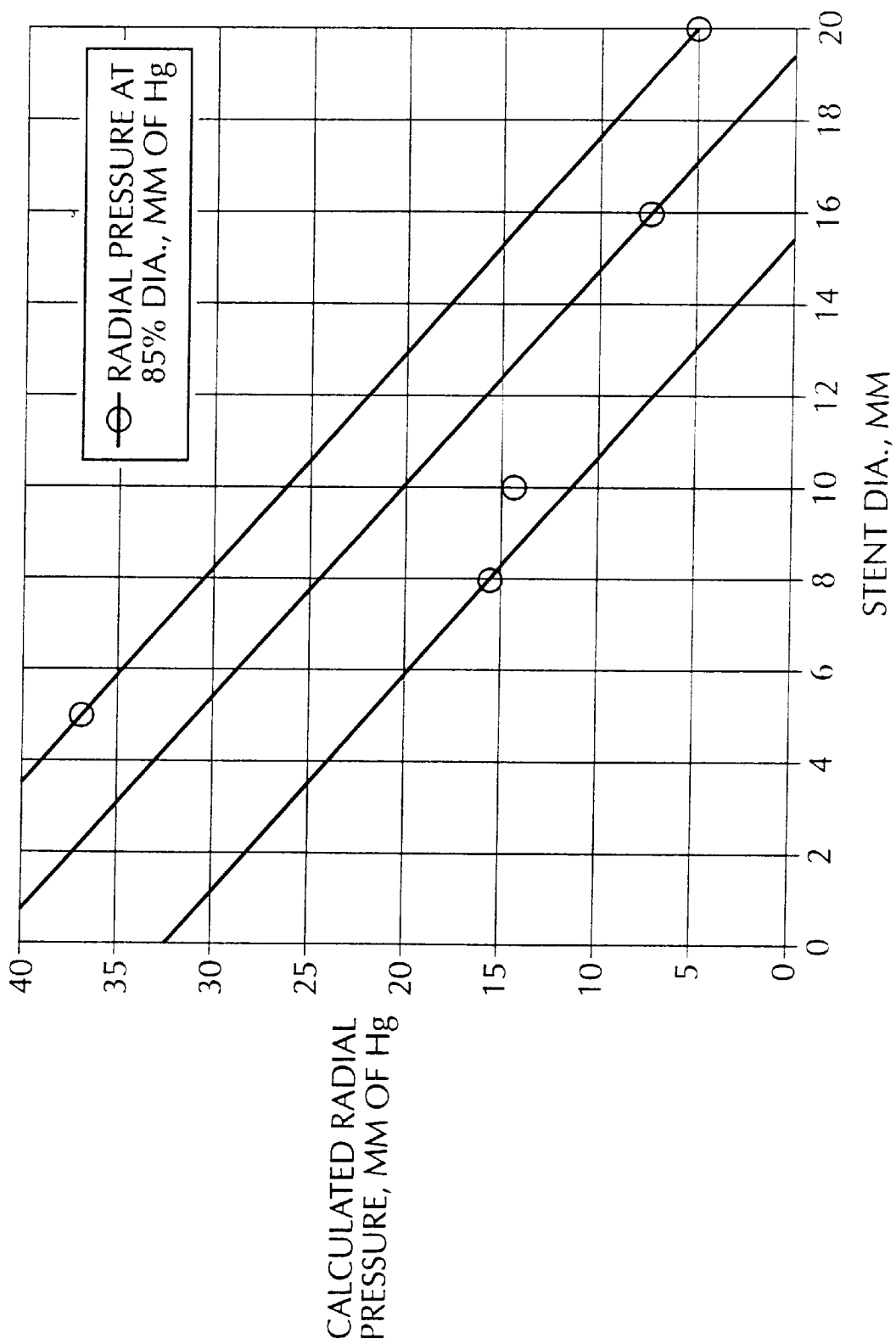
FIG. 16 is a graph of radial pressures as a function of diameter for a number of stents in accordance with the present invention.

From the information in FIG. 16, the average radial pressure as a function of diameter (D) for stents with relaxed or free state diameters of 5–16 mm can be characterized by Equation 1 below.

$$\text{Pressure [mm Hg]} = -2D[\text{mm}] + 40 \qquad \text{Eq. 1}$$

The range of radial pressures available for the 5–16 mm diameter stents is characterized by Equation 2 below.

$$\text{Pressure [mm Hg]} = -2D[\text{mm}] + 40 \pm 20 \qquad \text{Eq. 2}$$

A preferred range of radial pressures available for the 5–16 mm diameter stents is characterized by Equation 3 below.

$$\text{Pressure [mm Hg]} = -2D[\text{mm}] + 40 \pm 15 \quad \text{Eq. 3}$$

EXAMPLE 7

Stents 10 can be fabricated from a titanium alloy which consists of at least about 68% nd 1–29% of each aluminum (Al), tin (Sn), zirconium (Zr) and molybdenum (Mo). A preferred alloy having these constituents is Ti—6Al—2Sn—4Zr—6Mo. Wire composed of the Ti—6Al—2Sn—4Zr—6Mo alloy is commercially available from a number of sources including RMI Titanium of Niles, Ohio.

EXAMPLE 8

Stents 10 can be fabricated from a titanium alloy which consists of at least about 68% titanium and 1–28% of each aluminum (Al), vanadium (V), chromium (Cr), molybdenum (Mo) and zirconium (Zr). A preferred alloy having these constituents is Ti—3Al—8V—6Cr—4Mo—4Zr. Wire composed of the Ti—3Al—8V—6Cr—4Mo—4Zr alloy is commercially available from a number of sources including RMI Titanium of Niles, Ohio.

EXAMPLE 9

Stents 10 can be fabricated from a titanium alloy which consists of at least about 68% titanium and 1–31% of each aluminum (Al) and vanadium (V). Preferred alloys having these constituents are Ti—6Al—4V and Ti—6Al—4V ELI. Chemical, mechanical and metallurgical requirements for Ti—6AL—4V alloy for surgical implants are published in ASTM Standard Designation F 1472. Chemical, mechanical and metallurgical requirements for Ti—6AL—4V ELI alloy for surgical implants are published in ASTM Standard Designation F 620. Wire composed of the Ti—6Al—4V and Ti—6Al—4V ELI alloys is commercially available from a number of sources including RMI Titanium of Niles, Ohio.

EXAMPLE 10

Stents 10 can be fabricated from unalloyed titanium wire. Chemical, mechanical and metallurgical requirements for a number of grades of unalloyed titanium wire used for surgical implants are published in ASTM Standard Designation F 1341. Unalloyed titanium wire of these types is commercially available from a number of sources including RMI Titanium of Niles, Ohio.

EXAMPLE 11

Stents 10 can be fabricated from a wide variety of titanium alloys which contain at least about 68% titanium and which are substantially free of nickel, cobalt and chromium. A number of the alloys described in the examples given above have these characteristics. Commercially available alloys of these types typically have less than about 0.1% of nickel, cobalt, chromium and/or other elements.

EXAMPLE 12

Figure 17:
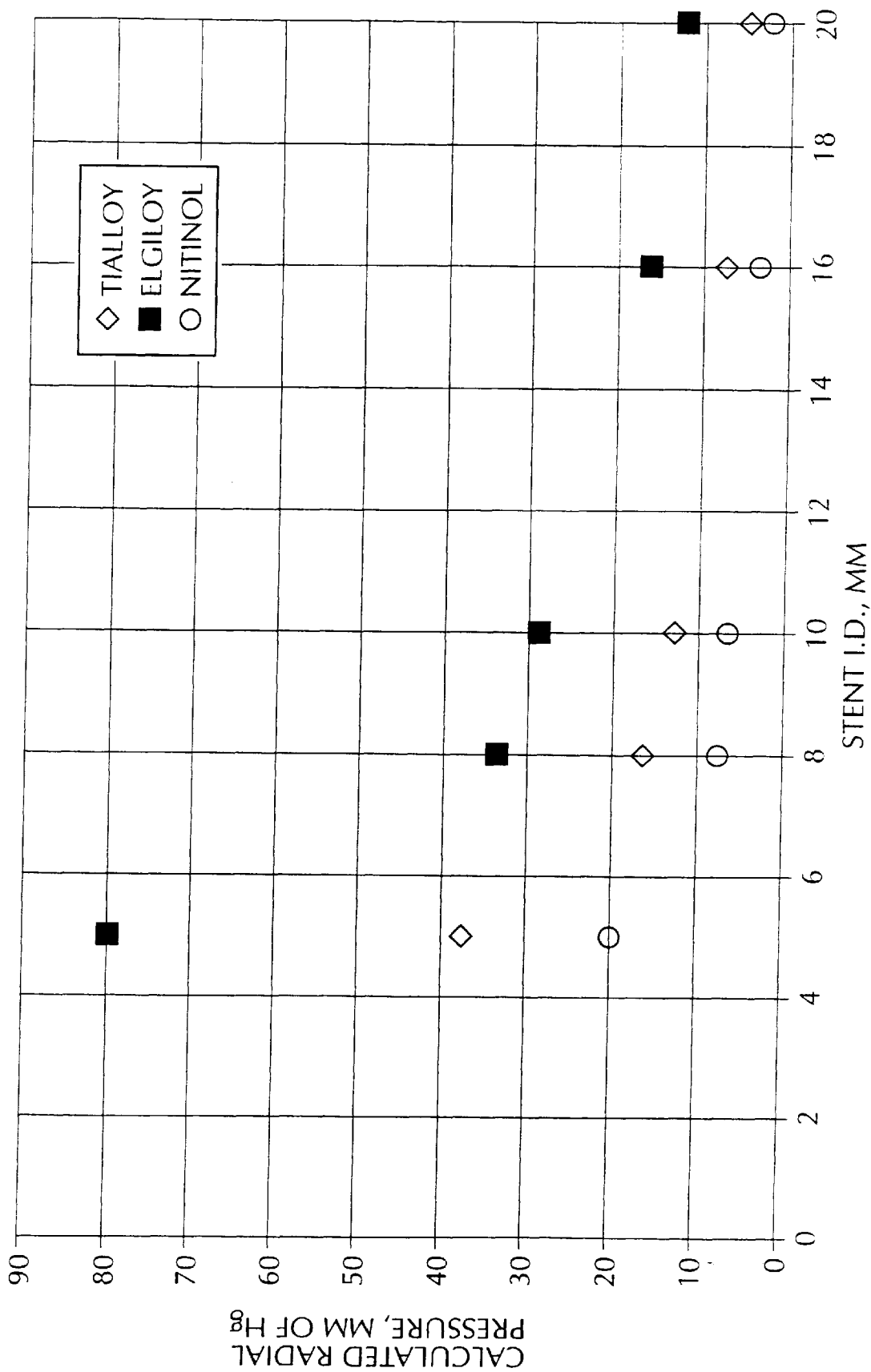
FIG. 17 is a graph of calculated radial pressures as a function of diameters for several stents formed from different materials.

FIG. 17 is a graph of calculated radial pressures as a function free state inner diameters for stents formed from Ti—6Al—4V alloy ("Ti alloy"), Elgiloy® alloy and Nitinol alloy. The radial pressures were calculated for stents having five, eight, ten, sixteen and twenty millimeter inner diameters at 85% of their free state diameter. The calculations were made using the formulas described in the Jedwab and Clerc article described above. From FIG. 17 it is evident that the radial pressures of the Ti alloy stents are about 0.4–0.5 times the radial pressures of similarly sized and configured Elgiloy® alloy stents. The radial pressures of the Ti alloy stents are about 1.8–1.9 times the radial pressures of similarly sized and configured Nitinol stents. Specifications of the stents described in FIG. 17 are set forth below in Table 2.

TABLE 2

| Diameter (mm) | Number of Wires | Braid Angle (degrees) | Wire Diameter (mm) |
|---|---|---|---|
| 5 | 20 | 110 | 0.09 |
| 8 | 24 | 110 | 0.11 |
| 10 | 24 | 105 | 0.14 |
| 16 | 30 | 110 | 0.17 |
| 20 | 36 | 120 | 0.17 |

FIGS. 4–6 are illustrations of a delivery device 20 for delivering stent 10 to a treatment site in a body vessel. As shown, stent 10 is carried by the distal portion of delivery device 20, and is placed on the delivery device in a radially contracted or compressed state. The proximal portion of delivery device 20 generally remains outside of the body for manipulation by the operator.

Delivery device 20 includes an elongated, inner tube 30, preferably having an axially extending lumen therethrough. The distal portion of inner tube 30 is flexible and can be made from nylon or other suitably flexible biocompatible polymeric material. At its distal end, inner tube 30 is provided with a head 31, through which the lumen continues. Head 31 serves to facilitate the insertion of delivery device 20 through a narrow opening in a body vessel. The proximal portion of inner tube 30 is preferably formed from stainless steel or other suitably rigid metal alloy. The proximal end of the distal portion of inner tube 30 is bonded to the distal end of the proximal portion of the inner tube in any conventional manner such as by using a standard adhesive.

A proximal tube 50 surrounds the proximal portion of inner tube 30 in coaxial fashion. Proximal tube 50 is preferably formed from polyurethane. The proximal end of tube 50 is connected to a valve body 40 having a side port 41. An extension tube 45 extends from side port 41 to an opening 42. This arrangement allows fluid to be injected through extension tube 45 and between proximal tube 50 and inner tube 30. A moveable hose 55 surrounds the distal portion of inner tube 30. Hose 55 is rolled over itself to form a double-walled section. The proximal end of inner wall 56 of a double-walled section is connected directly to inner tube 30. The proximal end of the outer wall 57 of the double-walled section is connected to the outer surface of the distal portion of proximal tube 50. These connections can be achieved by any conventional means such as by a standard adhesive. This arrangement allows hose 55 to be rolled off stent 10 and placed on the distal portion of inner tube 30. By moving valve body 40 in the proximal direction, outer wall 57 of hose 55 slides proximally over inner wall 56. This causes inner wall 56 to "roll back" off of stent 10. To facilitate movement of hose 55 off of stent 10, at least that portion of inner wall 56 that contacts outer wall 57 in the area where hose 55 is rolled over to form the double-walled section should be lubricous. The lubricous characteristic can be achieved by adding a lubricous substance to this surface of hose 55, injecting a lubricous liquid between inner wall 56 and outer wall 57 or forming hose 55 from a naturally slippery material such as Teflon coating.

In a preferred embodiment, at least the surfaces of inner wall 56 and outer wall 57 that face each other in the double-walled section are coated with a lubricous hydrophilic coating. In one embodiment the hydrophilic coating is 2018-M material available from Hydromer Inc. of Whitehouse, N.J. Other materials that can be used are polyethylene oxide and hyaluronic acid. When wet, the hydrophilic coating becomes lubricous and thus reduces friction between inner wall 56 and outer wall 57 of the double-walled section of hose 55 as outer wall 57 moves past inner wall 56. This facilitates the removal of the double-walled section of hose 55 from stent 10. In a preferred embodiment hydrophilic material is added to hose 55 during the assembly of delivery device 20. To enable the hydrophilic material to adequately bond to hose 55, the material used to manufacture hose 55 should be matched to the hydrophilic material used. It has been found that polyurethane works well as a material for hose 55. In particular, a blend of 65D and 75D polyurethane provides sufficient flexibility to allow hose 55 to roll over itself yet still be soft enough and compatible with the hydrophilic material that it can be properly coated. In one embodiment, the blend is formed of 50% 65D polyurethane and 50% 75D polyurethane.

During the assembly of delivery device 20, one side of hose 55 is coated with the hydrophilic material after the outer wall 57 of the hose has been connected to proximal tube 50. Isopropyl alcohol is first applied to one side of hose 55 to clean the surface and remove the waxy film resulting from the plasticizers in the polyurethane. The same side of hose 55 is then coated with the hydrophilic material. The surface of hose 55 should be flushed with alcohol for about thirty seconds. Similarly, the surface of hose 55 should be flushed with the hydrophilic coating for about thirty seconds. It has been found that this technique deposits sufficient hydrophilic material on inner wall 56 and outer wall 57 to allow hose 55 to be rolled back with minimal friction when the hydrophilic material is wet.

After delivery device 20 has been assembled and is ready for use, the hydrophilic coating is wetted with physiological saline solution by injecting the solution through extension tube 45, past proximal tube 50 and into the space between inner wall 56 and outer wall 57 of the double-walled section of hose 55. Excess fluid exits from the hole 59 formed toward the distal end of the double-walled section of hose 55. In this same manner, a lubricous fluid such as polyethylene glycol can be injected into the space between inner wall 56 and outer wall 57 of the double-walled section to provide the lubricous characteristic of hose 55 in place of adding a lubricous hydrophilic material through hose 55 as described above.

The manner by which delivery device 20 is operated to deliver stent 10 to a treatment site in a body vessel or lumen including curved sections is illustrated in FIGS. 7–10. As shown, stent 10 is placed in a radially compressed state in a surrounding relationship to the outer distal end of inner tube 30. Stent 10 is constrained on inner tube 30 by the double-walled section of hose 55. It is important that stent 10 not be confined too tightly on inner tube 30. Hose 55 should apply just enough force to stent 10 to hold stent 10 in place. The double-walled section of hose 55 can be removed from around stent 10 by pulling valve body 40 and proximal tube 50 in a proximal direction. The double-walled section "rolls" off stent 10. No sliding movements take place between stent 10 and inner wall 56 which contacts stent 10. Along with the movement of the double-walled section in a proximal direction, the distal end of stent 10 will be exposed in a radial direction to engagement against the wall of the body vessel. As the double-walled section of hose 55 continues moving proximally, more of stent 10 expands in a radial direction until the entire length of stent 10 is exposed and engages the wall of a body vessel.

Lumen 35 is used to enable delivery device 20 to follow a guide wire (not shown) previously inserted percutaneously into the body vessel. The lumen of inner tube 30 can also be used to introduce a contrast fluid to the area around the distal end of delivery device 20 so the position of delivery device 20 can be detected (e.g., through the use of fluoroscopy or X-ray techniques).

The stents of the present invention can be delivered by alternative methods or using alternative devices. For instance, the device described in Heyn et al. U.S. Pat. No. 5,201,757 can be utilized.

Figure 14:
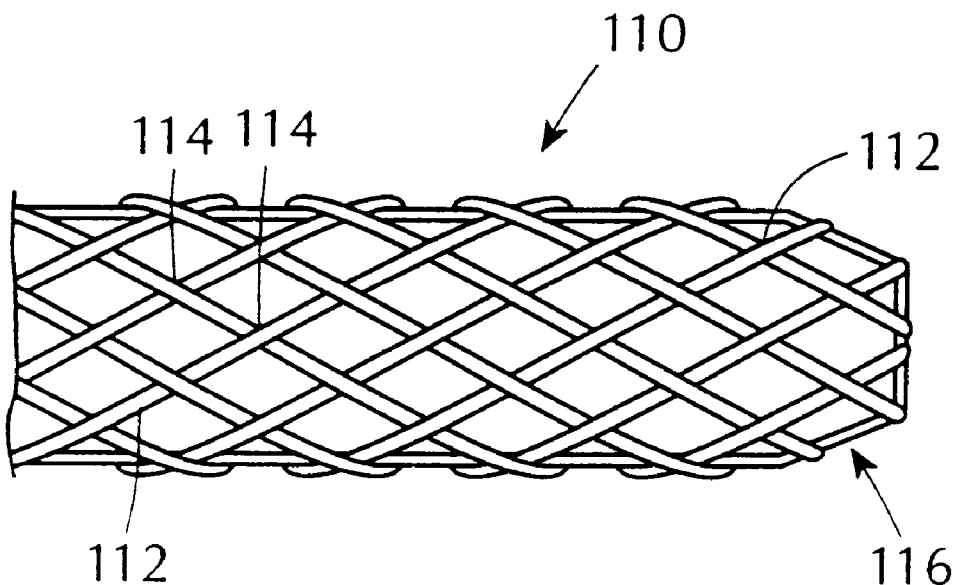
FIG. 14 is a side view of a second embodiment of a stent in accordance with the present invention.
Figure 15:
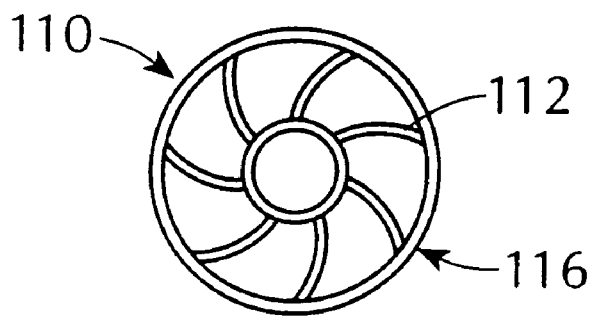
FIG. 15 is an end view of the stent shown in FIG. 14.

Another embodiment of the present invention, stent 110, is illustrated in FIGS. 14 and 15. Stent 110 is similar to stent 10 described above in that it is a tubular device formed from two sets of oppositely-directed, parallel, spaced-apart and helically wound elongated strands or filaments 112. The sets of filaments 112 are interwoven in an over and under braided configuration intersecting at points such as 114 to form an open mesh or weave construction. One end 116 of stent 110 is tapered and has a diameter which decreases from the diameter of the other portions of the stent to a reduced diameter. Stent 110 can be otherwise identical in structure and fabricated from the same titanium or titanium alloy materials as stent 10 described above. Stent 110 can be applied (in the manner of stent 10 described above) to a desired location within a vessel, for example, Vena Vava Inferior, for the purpose of preventing lung emboli. When used in this application, stent 110 can be inserted into Vena Cava with a high degree of precision and functions as a filter.

Stents 10 and 110 offer considerable advantages. In particular, the unalloyed titanium and titanium alloys from which they are formed are highly biocompatible and exhibit good resistance to thrombosis and bacteria adhesion. The stents have a relatively low elastic modulus and moderately high strength at given stress levels. They are therefore durable yet sufficiently flexible that they can be delivered to treatment sites through curved body vessels. The titanium stents 10 and 110 exert a gentler radial force against the lumen wall than would the current Elgiloy® stent. The radial force could be made to be higher or lower by utilizing larger or smaller diameter wire in the stent construction. The stents are also radiopaque, thereby enabling the devices to be visualized during implantation.

Although the present invention has been described with reference to preferred embodiments, those skilled in the art will recognize that changes can be made in form and detail without departing from the spirit and scope of the invention.

What is claimed is:

1. A method for treating a site within a vessel of a patient, including:
    providing a biocompatible medical device comprised of a tubular structure which is radially self-expandable between a compressed state and an expanded state and which substantially consists of titanium or titanium alloy characterized by a mean elongation less than or equal to 3.1% and includes at least about 68 weight percent titanium;
    providing a delivery system with the medical device positioned on a portion of the delivery system in the compressed state;
    inserting the portion of the delivery system with the medical device into the patient's vessel at a location spaced from the treatment site, and manipulating the delivery system to advance the medical device through the vessel, to the treatment site;

allowing the medical device to self-expand within the vessel; and removing the delivery system from the patient with the medical device remaining in the expanded state and supporting the vessel.

2. The method of claim 1 wherein providing the medical device includes providing a tubular structure which the titanium alloy consists essentially of at least about 68 weight percent titanium and at least one element selected from the group consisting of aluminum, tin, zirconium, molybdenum, chromium, niobium and vanadium.

3. The method of claim 2 wherein providing the medical device includes providing a tubular structure which the titanium alloy consists essentially of at least about 68 weight percent titanium, 1–31 weight percent niobium and 1–31 weight percent zirconium.

4. The method of claim 3 wherein providing the medical device includes providing a tubular structure in which the titanium alloy includes 10–15 weight percent niobium and 10–15 weight percent zirconium.

5. The method of claim 4 wherein providing the medical device includes providing a tubular structure in which the titanium alloy includes about 13 weight percent niobium and about 13 weight percent zirconium.

6. The method of claim 3 wherein providing the medical device includes providing a tubular structure in which the titanium alloy consists essentially of at least about 68 weight percent titanium, 1–29 weight percent aluminum, 0.5–29 weight percent tin, 1–29 weight percent zirconium and 1–29 weight percent molybdenum.

7. The method of claim 6 wherein providing the medical device includes providing a tubular structure in which the titanium alloy includes about 6 weight percent aluminum, about 2 weight percent tin, about 4 weight percent zirconium and about 4 weight percent molybdenum.

8. The method of claim 3 wherein providing the medical device includes providing a tubular structure in which the titanium alloy consists essentially of at least about 68 weight percent titanium, 1–28 weight percent aluminum, 1–28 weight percent vanadium, 1–28 weight percent chromium, 1–28 weight percent zirconium and 1–28 weight percent molybdenum.

9. The method of claim 8 wherein providing the medical device includes providing a tubular structure in which the titanium alloy includes about 3 weight percent aluminum, about 8 weight percent vanadium, about 6 weight percent chromium, about 4 weight percent zirconium and about 4 weight percent molybdenum.

10. The method of claim 3 wherein providing the medical device includes providing a tubular structure in which the titanium alloy consists essentially of at least about 68 weight percent titanium, 1–31 weight percent aluminum, and 1–31 weight percent vanadium.

11. The method of claim 10 wherein providing the medical device includes providing a tubular structure in which the titanium alloy includes about 6 weight percent aluminum and about 4 weight percent vanadium.

12. The method of claim 1 wherein providing the medical device includes providing a tubular structure in which the titanium alloy is substantially free of nickel.

13. A method for treating a site within a vessel of a patient, including:

providing a biocompatible medical device comprised of a tubular structure which is radially expandable from a reduced-diameter compressed state to an expanded state and which substantially consists of titanium alloy including at least about 68 weight percent titanium, and characterized by a mean elongation less than or equal to 3.1%;

providing a delivery system with medical device positioned on a portion of the delivery system in the compressed state;

inserting the portion of the delivery system with the medical device into the patient's vessel and advancing the medical device through the vessel to the treatment site;

actuating the delivery system to expand the medical device to the expanded state within the vessel; and removing the delivery system from the patient with the medical device remaining in the expanded state and supporting the vessel.

14. The method of claim 13 wherein providing the medical device includes providing a tubular structure in which the titanium alloy includes between about 68 weight percent titanium and 96 weight percent titanium.

15. The method of claim 14 wherein providing the medical device includes providing a tubular structure in which the titanium alloy consists essentially of at least about 68 weight percent titanium and at least one element selected from the group consisting of aluminum, tin, zirconium, molybdenum, chromium, niobium and vanadium.

16. The method of claim 15 wherein providing the medical device includes providing a tubular structure in which the titanium alloy consists essentially of at least about 68 weight percent titanium, 1–31 weight percent niobium and 1–31 weight percent zirconium.

17. The method of claim 16 wherein providing the medical device includes providing a tubular structure in which the titanium alloy includes 10–15 weight percent niobium and 10–15 weight percent zirconium.

18. The method of claim 17 wherein providing the medical device includes providing a tubular structure in which the titanium alloy includes about 13 weight percent niobium and about 13 weight percent zirconium.

19. The method of claim 15 wherein providing the medical device includes providing a tubular structure in which the titanium alloy consists essentially of at least about 68 weight percent titanium, 1–29 weight percent aluminum, 0.5–29 weight percent tin, 1–29 weight percent zirconium and 1–29 weight percent molybdenum.

20. The method of claim 19 wherein providing the medical device includes providing a tubular structure in which the titanium alloy includes about 6 weight percent aluminum, about 2 weight percent tin, about 4 weight percent zirconium and about 4 weight percent molybdenum.

21. The method of claim wherein providing the medical device includes providing a tubular structure in which the titanium alloy consists essentially of at least about 68 weight percent titanium, 1–28 weight percent aluminum, 1–28 weight percent vanadium, 1–28 weight percent chromium, 1–28 weight percent zirconium and 1–28 weight percent molybdenum.

22. The method of claim 21 wherein providing the medical device includes providing a tubular structure in which the titanium alloy includes about 3 weight percent aluminum, about 8 weight percent vanadium, about 6 weight percent chromium, about 4 weight percent zirconium and about 4 weight percent molybdenum.

23. The method of claim 15 wherein providing the medical device includes providing a tubular structure in which the titanium alloy consists essentially of at least about 68 weight percent titanium) 1–31 weight percent aluminum, and 1–31 weight percent vanadium.

24. The method of claim 23 wherein providing the medical device includes providing a tubular structure in which the titanium alloy includes about 6 weight percent aluminum and about 4 weight percent vanadium.

25. The method of claim 14 wherein providing the medical device includes providing a tubular structure in which the titanium alloy is substantially free of nickel.

\* \* \* \* \*

UNITED STATES PATENT AND TRADEMARK OFFICE
CERTIFICATE OF CORRECTION

PATENT NO : 6,183,508
DATED : February 6, 2001
INVENTOR(S) : Jonathan S. Stinson It is certified that error appears in the above-identified patent and that said Letters Patent are hereby corrected as shown below:

On the cover page, the correct name of the assignee should be "Schneider (USA) Inc"

Column 12, line 6, after "with" insert --the--

Column 12, line 52, after "claim" insert --15--

Column 13, line 4, after "titanium" delete ")" and insert therefor --,--

Signed and Sealed this

Twenty-ninth Day of May, 2001

*Attest:*

NICHOLAS P. GODICI

*Attesting Officer*     *Acting Director of the United States Patent and Trademark Office*